United States Patent [19]

Michaely et al.

[11] Patent Number: 4,623,384

[45] Date of Patent: Nov. 18, 1986

[54] BENZYLACRYLARYL AMIDE HERBICIDAL COMPOUNDS AND METHODS OF USE

[75] Inventors: William J. Michaely, Richmond; Christopher Knudsen, Berkeley, both of Calif.

[73] Assignee: Stauffer Chemical Co., Westport, Conn.

[21] Appl. No.: 822,344

[22] Filed: Jan. 24, 1986

Related U.S. Application Data

[63] Continuation-in-part of Ser. No. 740,653, Jun. 3, 1985, abandoned.

[51] Int. Cl.$^4$ ...................... A01N 37/34; C07C 121/78
[52] U.S. Cl. ........................................ 71/105; 558/392
[58] Field of Search ........................... 71/105; 558/392

[56]  References Cited

U.S. PATENT DOCUMENTS

| | | | |
|---|---|---|---|
| 3,079,366 | 2/1963 | Boyle et al. | 558/392 X |
| 3,656,932 | 4/1972 | Scheuermann et al. | 71/105 |
| 3,981,717 | 9/1976 | Walworth | 71/105 |

Primary Examiner—Dolph H. Torrence
Attorney, Agent, or Firm—Michael J. Bradley

[57]  ABSTRACT

A compound having the structural formula

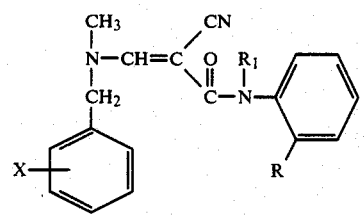

wherein R is halogen, including fluorine, chlorine, bromine and iodine, preferably chlorine; methyl, ethyl, ethenyl, methoxy, nitro, trifluoromethyl or cyano; $R_1$ is hydrogen, methyl, ethyl, or allyl; and X is in either the 2- or 3-position and is hydrogen, 2-methyl, 3-methyl, 2-chlorine, 3-chlorine, 2-fluorine, 3-fluorine or 2-methoxy and their use as postemergent herbicides.

27 Claims, No Drawings

BENZYLACRYLARYL AMIDE HERBICIDAL COMPOUNDS AND METHODS OF USE

CROSS REFERENCE TO RELATED APPLICATIONS

This application is a continuation-in-part of application Ser. No. 740,653, filed June 3, 1985, abandoned.

BACKGROUND OF THE INVENTION

The present invention relates to certain benzylacrylaryl amide compounds which are useful as post-emergent herbicides against annual and perennial grasses and broadleaf weeds.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

Many arylacryl esters have been disclosed in the prior art [Huppatz, John L. et al., *Agric. Biol. Chem.*, 1982, 45(12), 2769–73 (Eng.)]. Several related arylacrylaryl amides have also been disclosed [Wolfbeis, Otto S., *Chem. Ber.*, 1981, 114(11), 3471–84] but no criticality of substitution patterns has been disclosed to result in highly active postemergent herbicides such as those disclosed and claimed in this application.

Efforts are constantly being made, however, to find compounds which are equal to or greater in effectiveness than presently existing compounds, or which are more economical to produce.

DESCRIPTION OF THE INVENTION

This invention relates to the production of novel arylacrylaryl amide compounds and their use as herbicides. The novel compounds of this invention have the following structural formula

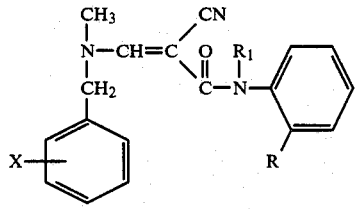

wherein

R is halogen, including fluorine, chlorine, bromine and iodine, preferably chlorine; methyl, ethyl, ethenyl, methoxy, nitro, trifluoromethyl or cyano;

$R_1$ is hydrogen, methyl, ethyl, or allyl; and

X is in either the 2- or 3-position and is hydrogen, 2-methyl, 3-methyl, 2-chlorine, 3-chlorine, 2-fluorine, 3-fluorine or 2-methoxy.

The compounds of the invention can be produced in a multi-step process in accordance with the following generalized sequence of steps. R, $R_1$, and X are as defined above.

Reaction No. 1

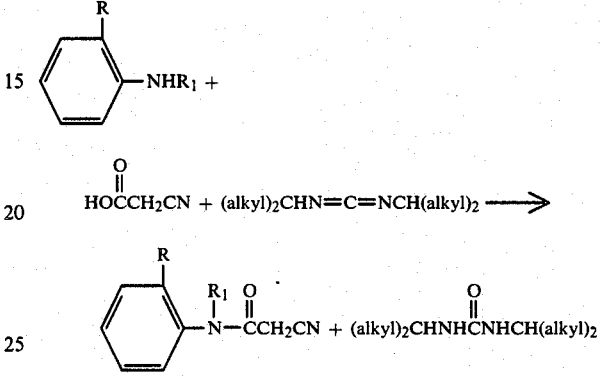

Generally, a 1.1 mole amount of a carbodiimide, dissolved in a one-to-one ratio of tetrahydrofuran and acetonitrile, is added to a mixture of one mole each of the substituted aniline and cyanoacetic acid in the same solvent system. The mixture is stirred at room temperature for about 20 hours. Water (0.1 mole) is added and the mixture filtered. The product is dried over $MgSO_4$, filtered and the solvent evaporated.

Reaction No. 2

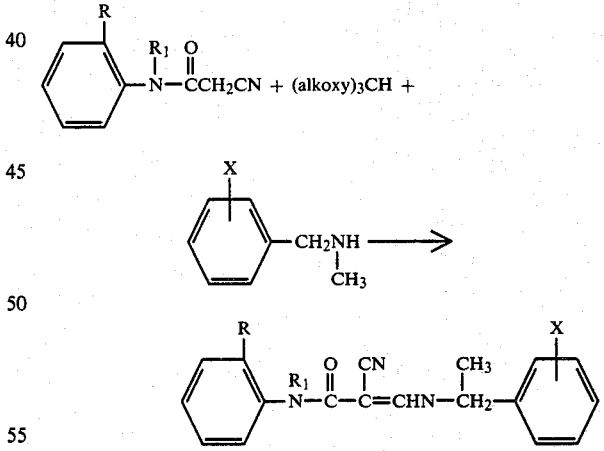

A mole amount each of the benzylamine and the reaction product from Reaction No. 1 are combined with 3.5 moles of a trialkoxyorthocarboxylate. The mixture is heated for one hour while low boiling reaction products are distilled. The final product is purified by triturating in ether, filtering and air drying.

The example below illustrates methods of making the compounds of the invention using various starting materials. All intermediates and final products were identified by infrared, nuclear magnetic resonance and proton magnetic resonance spectroscopy.

EXAMPLE

Preparation of 2-Cyano-3-[N-(2-chlorobenzyl)-N-methylamino]-N-(2-chlorophenyl)acrylamide Step 1: Into a stirred solution of 25 grams (g) (200 mmol) o-chloroaniline in 500 ml methylene chloride, 20 grams (9.9 mmol) of bromoacetyl bromide was added dropwise and the resulting reaction mixture was let stand one hour. The solution was extracted two times with 1N HCl and the organic phase was reduced on a rotary evaporator.

The wet amide was dissolved in about 300 ml p-dioxane and 5.8 g (119 mmol) NaCN (sodium cyanide) and 80 ml water was added to it. The solution was slowly heated to reflux, then after two hours the solution was cooled and partially reduced on the rotary evaporator. $Et_2O$ was added to the residue and the organic layer was extracted with water, dryed over $MgSO_4$ and concentrated on the rotary evaporator to yield 17.1 g (88 mmol) of N-(2-chlorophenyl)-2-cyanoacetamide.

Step 2: A mixture of 18.3 g of the cyanoamide product of Step 1, 13.3 g (89 mmol) of triethylorthoformate and 18.1 g (178 mmole) of acetic anhydride in a round-bottom flask was heated and reacted in an oil bath at 150° C. The ethyl acetate produced was collected by simple distillation. After one hour of reaction time more triethylorthoformate (3.3 g, 122 mmol) and acetic anhydride (4.5 g, 44 mmol) was added and heated as above.

A very dark solid was produced on cooling the reaction mixture. The solid was recrystallized in an ethanol/ether solvent to give 6.4 g (28 mmol) (29% yield) of a brown solid.

A portion of the brown solid (1.5 g, 6.7 mmol) and N-methyl-2-chlorobenzylamine (1.1 g, 7.2 mmol) were mixed and heated to 80° for one minute. The resulting solid was collected by filtration and washed with ether to yield 1.87 g (52%) of an off-white solid having a melting point of 138°–139° C.

This compound will be referred to as Compound No. 7 throughout the remainder of the specification.

The following is a table of certain selected compounds that are preparable according to the procedure described herein. Compound numbers are assigned to each compound and are used throughout the remainder of the application.

TABLE I

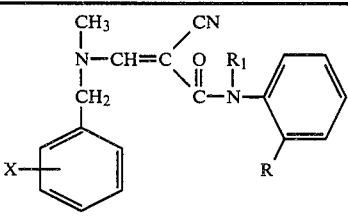

| Compound Number | R | R1 | X | $n_D^{30}$ or melting point °C. |
|---|---|---|---|---|
| 1 | —Cl | —H | —H | 111–113 |
| 2 | —Cl | —H | 3-Cl | 85–86 |
| 3 | —I | —H | —H | 172–174 |
| 4 | —Br | —H | —H | 148–150 |
| 5 | —NO2 | —H | —H | 101–103 |
| 6 | —Cl | —CH3 | —H | |
| 7 | —Cl | —H | 2-Cl | 138–139 |
| 8 | —Cl | —H | 2-F | 80–82 |
| 9 | —Cl | —H | 2-CH3 | 125–127 |
| 10 | —CF3 | —H | —H | 100–101 |
| 11 | —OCH3 | —H | —H | 113–114 |
| 12 | —F | —H | —H | 93–94 |
| 13 | —CH3 | —H | —H | 113–115 |
| 14 | —CN | —H | —H | 109–113 |
| 15 | —Cl | —H | 3-CH3 | 85–87 |
| 16 | —Cl | —H | 3-F | 68–70 |
| 17 | —Cl | —H | 2-OCH3 | 83–85 |
| 18 | —Cl | —CH2CH3 | —H | 99–102 |
| 19 | —I | —CH3 | —H | |
| 20 | —CH=CH2 | —H | —H | |

Herbicidal Screening Tests

As previously mentioned, the compounds described herein produced in the manner above-described are phytotoxic compounds which are useful and valuable in controlling various plant species. Selected compounds of this invention were tested as herbicides in the following manner.

Post-emergence herbicide test. Seven grass and broadleaf weed species, including green foxtail (FT) (*Setaria viridis*), watergrass (WG) (*Echinochloa crusgalli*), wild oat (WO) (*Avena fatua*), annual morningglory (AMG) (*Ipomoea purpurea*), velvetleaf (VL) (*Abutilon theophrasti*), mustard (MD) (*Brassica kaber*) and curly dock (CD) (*Rumex crispus*), are seeded in individual rows in 6×10×3 inch flats. The flats are placed in the greenhouse, watered daily (both before and after chemical treatment) with a sprinkler and maintained at about 78° F. Chemical spray tratment is made 12 days after planting. The spray is prepared by weighing out 333 mg of compound and dissolving it in 25 ml acetone containing 1% polyoxyethylene sorbitan monolaurate emulsifier. From this stock solution 18 ml are removed and brought up to a 40 ml volume with a 19:1 water/acetone mixture. The carrier volume is 80 gallons/A (748 L/ha) and a 4 lb/A (4.48 kg/ha) rate is used.

Watering of the treated flats is confined to the soil surface and not to the foliage of the sprouted plants. Twelve to fourteen days after treatment, the degree of injury or control is determined by comparison with untreated plants of the same age. The injury rating from 0 to 100% is recorded for each species as percent control with 0% representing no injury and 100% representing complete control.

The results of the post-emergence herbicide test are reported in Table II.

TABLE II

Post-Emergence Herbicidal Activity
Application Rate - 4.48 kg/ha

| Cmpd. No. | FT | WG | WO | AMG | VL | MD | CD | AVE GR | AVE BL |
|---|---|---|---|---|---|---|---|---|---|
| 1 | 40 | 40 | 10 | 100 | 100 | 100 | 20 | 30 | 80 |
| 2 | 100 | 45 | 35 | 35 | — | 100 | 70 | 60 | 68 |
| 3 | 10 | 0 | 0 | 0 | — | 15 | 0 | 7 | 5 |
| 4 | 40 | 60 | 60 | 50 | 70 | 20 | 100 | 53 | 60 |
| 5 | 65 | 40 | 70 | 45 | 60 | 60 | 25 | 58 | 48 |
| 6 | 90 | 40 | 20 | 45 | 65 | 90 | 100 | 50 | 75 |
| 7 | 20 | 30 | 0 | 15 | 65 | 55 | 20 | 17 | 39 |
| 8 | 100 | 100 | 100 | 100 | 80 | 100 | 100 | 100 | 95 |
| 9 | 100 | 85 | 80 | 100 | 70 | 95 | 70 | 88 | 84 |
| 10 | 100 | 35 | 30 | 30 | — | 100 | 70 | 55 | 67 |
| 11 | 80 | 0 | 0 | 25 | — | 20 | 0 | 27 | 15 |
| 12 | 90 | 20 | 20 | 70 | — | 100 | 60 | 43 | 77 |
| 13 | 100 | 10 | 10 | 50 | — | 95 | 10 | 40 | 52 |
| 14 | 100 | 85 | 40 | 100 | — | 100 | 90 | 75 | 97 |
| 15 | 20 | 0 | 0 | 20 | 40 | 85 | 30 | 7 | 44 |
| 16 | 100 | 40 | 0 | 100 | 100 | 100 | 100 | 47 | 100 |
| 17 | 60 | 0 | 0 | 20 | 70 | 90 | 0 | 20 | 45 |
| 18 | 0 | 0 | 0 | 25 | 0 | 5 | 0 | 0 | 25 |
| 19 | 15 | 10 | 0 | 20 | 25 | 20 | 0 | 8 | 16 |
| 20 | 0 | 0 | 0 | 20 | 0 | 90 | 0 | 0 | 28 |

AVE GR = The average of all grass weeds treated at the application rate.
AVE BL = The average of all broadleaf weeds treated at the application rate.

The compounds of the present invention are useful as herbicides, especially as post-emergence herbicides, and can be applied in a variety of ways at various concentrations. In practice, the compounds described herein are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for post-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the weeds either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable formulation is ultimately applied to the soil as a dispersion in water or other liquid. These granules are dust-free and free flowing when dry and yet upon dilution in water, form homogeneous dispersions. Typical carriers for dry flowables include fuller's earth, kaolin clays, silicas and other readily available wet organic or inorganic diluents. The dry flowables normally are prepared to contain 5% to about 95% of the active ingredient and usually contains a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and/or other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
|---|---|---|---|
| Ingredient | Weight % | | |
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis(3-methoxypropylamino)-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorobenzoic acid; thiocarbamates such as S-propyl N,N-dipropylthiocarbamate, S-ethyl N,N-dipropylthiocarbamate, S-ethyl cyclohexylethylthiocarbamate, S-ethyl hexahydro-1H-azepine-1-carbothioate and the like; anilines such as 4-(methylsulfonyl)-2,6-dinitro-N,N-substituted aniline, 4-trifluoromethyl-2,6-dinitro-N,N-di-n-propyl aniline, 4-trifluoromethyl-2,6-dinitro-N-ethyl-N-butyl aniline, 2-[4-(2,4-dichlorophenoxy)phenoxy]propanoic acid, 2-[1-(ethoxyimino)-butyl]-5-[2-ethylthio)propyl]-3-hydroxy-2-cyclohexene-1-one, (±)-butyl-2-[4-[(5-trifluoromethyl)-2-pyridinyl)oxy]phenoxy]propanate, sodium 5-[2-chloro-4-(trifluoromethyl)phenoxy]-2-nitrobenzoate, 3-isopropyl-1H-2,1,3-benzothiadiazine-4(3H)-one-2,2-dioxide, and 4-amino-6-tert-butyl-3-(methylthio)-as-triazin-5(4H)-one or (4-amino-6-(1,1-dimethylethyl)-3-(methylthio)-1,2,4-triazin-5(4H)-one). Fertilizers useful in combination with the active ingredients include, for example, ammonium nitrate, urea and superphosphate. Other useful additaments include materials in which plant organisms take root and grow such as compost, manure, humus, sand, and the like.

We claim:

1. A compound having the structural formula

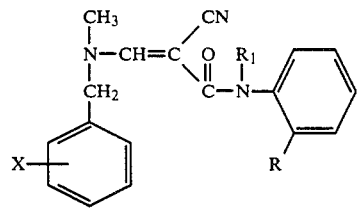

wherein R is selected from the group consisting of fluorine, chlorine, bromine, iodine, methyl, ethyl, ethenyl, methoxy, nitro, trifluoromethyl and cyano;

$R_1$ is selected from the group consisting of hydrogen, methyl, ethyl and allyl; and X is selected from the group consisting of a 2- or 3-fluorine, chlorine, methyl, hydrogen and 2-methoxy.

2. The compound of claim 1 wherein R is chlorine, $R_1$ is hydrogen and X is hydrogen.

3. The compound of claim 1 wherein R is chlorine, $R_1$ is hydrogen and X is hydrogen.

4. The compound of claim 1 wherein R is bromine, and $R_1$ and X are hydrogen.

5. The compound of claim 1 wherein R is nitro and $R_1$ and X are hydrogen.

6. The compound of claim 1 wherein R is chlorine, $R_1$ is methyl and X is hydrogen.

7. The compound of claim 1 wherein R is chlorine, $R_1$ is hydrogen and X is 2-fluorine.

8. The compound of claim 1 wherein R is chlorine, $R_1$ is hydrogen and X is 2-methyl.

9. The compound of claim 1 wherein R is trifluoromethyl and $R_1$ and X are hydrogen.

10. The compound of claim 1 wherein R is fluorine and $R_1$ and X are hydrogen.

11. The compound of claim 1 wherein R is methyl and $R_1$ and X are hydrogen.

12. The compound of claim 1 wherein R is cyano and $R_1$ and X are hydrogen.

13. The compound of claim 1 wherein R is chlorine, $R_1$ is hydrogen and X is 3-fluorine.

14. A herbicidal composition comprising an herbicidally effective amount of a compound having the structural formula

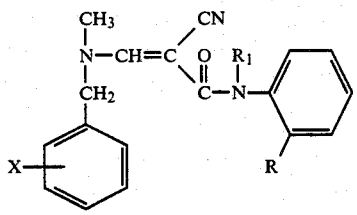

wherein R is selected from the group consisting of fluorine, chlorine, bromine, iodine, methyl, ethyl, ethenyl, methoxy, nitro, trifluoromethyl and cyano;
$R_1$ is selected from the group consisting of hydrogen, methyl, ethyl and allyl; and
X is selected from the group consisting of a 2- or 3-fluorine, chlorine, methyl, hydrogen and 2-methoxy; and an inert carrier.

15. The method of controlling undesirable vegetation comprising applying to the area where control is desired, an herbicidally effective amount of a compound having the formula

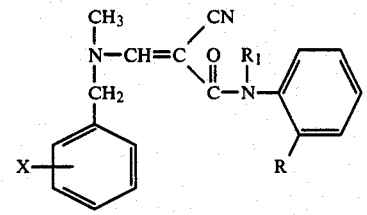

wherein R is selected from the group consisting of fluorine, chlorine, bromine, iodine, methyl, ethyl, ethenyl, methoxy, nitro, trifluoromethyl and cyano;
$R_1$ is selected from the group consisting of hydrogen, methyl, ethyl and allyl; and
X is selected from the group consisting of a 2- or 3-fluorine, chlorine, methyl, hydrogen and 2-methoxy.

16. The method of claim 15 wherein R is chlorine, $R_1$ is hydrogen and X is hydrogen.

17. The method of claim 15 wherein R is chlorine, $R_1$ is hydrogen and X is hydrogen.

18. The method of claim 15 wherein R is bromine, and $R_1$ and X are hydrogen.

19. The method of claim 15 wherein R is nitro and $R_1$ and X are hydrogen.

20. The method of claim 5 wherein R is chlorine, $R_1$ is methyl and X is hydrogen.

21. The method of claim 15 wherein R is chlorine, $R_1$ is hydrogen and X is 2-fluorine.

22. The method of claim 15 wherein R is chlorine, $R_1$ is hydrogen and X is 2-methyl.

23. The method of claim 15 wherein R is trifluoromethyl and $R_1$ and X are hydrogen.

24. The method of claim 15 wherein R is fluorine and $R_1$ and X are hydrogen.

25. The method of claim 15 wherein R is methyl and $R_1$ and X are hydrogen.

26. The method of claim 15 wherein R is cyano and $R_1$ and X are hydrogen.

27. The method of claim 15 wherein R is chlorine, $R_1$ is hydrogen and X is 3-fluorine.

* * * * *